(12) United States Patent
Clark

(10) Patent No.: US 6,174,285 B1
(45) Date of Patent: Jan. 16, 2001

(54) 3-D ULTRASOUND IMAGING SYSTEM WITH PRE-SET, USER-SELECTABLE ANATOMICAL IMAGES

(75) Inventor: David W. Clark, Windham, NH (US)

(73) Assignee: Agilent Technologies, Inc., Palo Alto, CA (US)

(*) Notice: Under 35 U.S.C. 154(b), the term of this patent shall be extended for 0 days.

(21) Appl. No.: 09/243,312

(22) Filed: Feb. 2, 1999

(51) Int. Cl.[7] .................................................. A61B 8/00
(52) U.S. Cl. ................................. 600/443; 128/916
(58) Field of Search .............................. 600/440, 441, 600/443, 447, 463, 467; 128/916

(56) References Cited

U.S. PATENT DOCUMENTS

| | | |
|---|---|---|
| 5,159,931 | 11/1992 | Pini ...................................... 128/660 |
| 5,315,999 | 5/1994 | Kinicki et al. . |
| 5,497,776 * | 3/1996 | Yamazaki et al. ............... 128/916 X |
| 5,538,003 | 7/1996 | Gadonniex et al. . |
| 5,817,019 * | 10/1998 | Kawashima ......................... 600/437 |
| 5,891,030 * | 4/1999 | Johnson et al. .................. 128/920 X |
| 5,957,844 * | 9/1999 | Dekel et al. .......................... 600/439 |
| 5,964,707 * | 10/1999 | Fenster et al. ...................... 600/443 |

* cited by examiner

Primary Examiner—Francis J. Jaworski

(57) ABSTRACT

An ultrasound imaging system incorporating the invention enables a user to select a pre-set anatomical view that is not available from standard ultrasound transducer imaging positions. The system includes a transducer which produces an ultrasound beam that acquires a 3-D set of echo signals. A processor enables the system user to be presented with a listing of pre-set anatomical views and is responsive to user selection of one of the pre-set views to control a converter within the system to derive from the 3-D set of echo signals, an image data set which, when displayed, presents the pre-set anatomical view selected by the user. In the preferred embodiment, at least some of the pre-set anatomical views are those that are not otherwise available from the standard transducer imaging positions.

27 Claims, 4 Drawing Sheets

3-D ULTRASOUND IMAGING SYSTEM WITH PRE-SET, USER-SELECTABLE ANATOMICAL IMAGES

FIELD OF THE INVENTION

This invention relates to 3-dimensional (3-D) ultrasound imaging systems and, more particularly, to an ultrasound imaging system which presents to the user a listing of available pre-set views that may be selected and enabled without the need for additional user inputs.

BACKGROUND OF THE INVENTION

Clinical practitioners have developed standard views for 2-D ultrasound imaging which remove much of the operator and view variability and speed up image acquisition and review. This is particularly true for trans-thoracic echocardiography, where there are only a few "windows" past the ribs and lungs which allow good image acquisition. The echocardiology standard views are illustrated in FIGS. 1a–1c and include the parasternal long axis view (FIG. 1a), the parasternal short axis view (FIG. 1b) and the apical 4-chamber view (FIG. 1c). The operator typically moves through a sequence of such standard views, putting the ultrasound transducer on the patient in standard places and with standard orientations. Thereafter, slight adjustments of the transducer position are made by the operator, based upon the displayed image.

The provision of standard views is highly useful to the practitioner as it enables recognition of differences between subsequent standard views, without requiring the practitioner to initially determine from what aspect ratio the view has been derived. See U. S. Pat. 5,315,999 to Kinicki et al., assigned to the same assignee as this Application, for further discussion re: preset imaging modes and parameters therefor.

Notwithstanding the obvious usefulness of 2-D imaging, such systems provide only a limited number of views of many organs, e.g., the heart. Recently, 3-D ultrasound systems have been introduced which acquire data for many different views from a single placement of a transducer on the patient. In such case, the view may be a 2-D slice, a 3-D rendering or another view derived from the data. A potential advantage of 3-D view acquisition is that the view can be optimized for the anatomy, rather than being fixed relative to the transducer. To accomplish 3-D imaging, a 3-D data set of image echo values is accumulated and subsequently processed to provide the desired view presentation. The process of acquiring a 2-D view from a 3-D data set is well known and need not be further elaborated.

As indicated above, FIGS. 1a–1c illustrate schematic showings of ultrasound heart images, given a positioning of the ultrasound transducer at one of the: apical, parasternal, suprasternal or subcostal imaging positions. Such views are: "standard" and provide showings of the long-axis view (FIG. 1a), the short axis view (FIG. 1b) and the 4-chamber view (FIG. 1c). The provision of such standard views enables ready diagnosis by the practitioner. As is known, however, certain features of the heart cannot be imaged using 2-D imaging systems. More specifically, features like face-on views of the pulmonary valve (shown in FIG. 2a in its open state), the aortic valve (shown in FIG. 2b in its closed state), and the mitral valve (shown in FIG. 2c in its closed state) cannot be directly imaged. To provide such views, the user must employ a 3-D ultrasound system.

Present implementations of 3-D ultrasound systems offer essentially only two methods for selecting a view. The first method provides a view which is derived from a simple fixed orientation relative to the transducer, such as an orthogonal 2-D slice. A second method is totally arbitrary and under explicit manual control of the operator. Such control is complicated and tedious due to the many parameters to be specified. For instance, many arbitrary views are constructed in an iterative, trial and error fashion, long after data acquisition. Some of the parameters which require operator adjustment and control are: orientation, viewpoint, bounding region, magnification, rendering technique, etc., etc.

Accordingly, the derivation of such a 3-D view is a slow and tedious process. Therefore, it is usually performed on an "off-line" computer system so as to avoid occupying a valuable ultrasound system during a period when it could be in use deriving further patient diagnostic views.

Therefore, a need exists for a clinical ultrasound imaging system which reduces the complexities facing the operator when obtaining a desired anatomical view from a 3-D data set. Further, certain 2-D anatomical views are diagnostically useful but cannot be readily obtained from standard ultrasound transducer imaging positions. The automatic availability of such views from 3-D data sets, on a real time basis, would be extremely useful from a diagnostic point of view.

SUMMARY OF THE INVENTION

An ultrasound imaging system incorporating the invention enables a user to select a pre-set anatomical view from a 3-D data set. The system includes a transducer which produces an ultrasound beam that acquires a 3-D set of echo signals. A processor enables the system user to be presented with a listing of pre-set anatomical views and is responsive to user selection of one of the pre-set views to control a converter within the system to derive from the 3-D set of echo signals, an image data set which, when displayed, presents the selected pre-set anatomical view. In the preferred embodiment, at least some of the pre-set anatomical views are those that are not otherwise available from the standard transducer imaging positions.

DETAILED DESCRIPTION OF THE PREFERRED EMBODIMENTS

Figure 3:
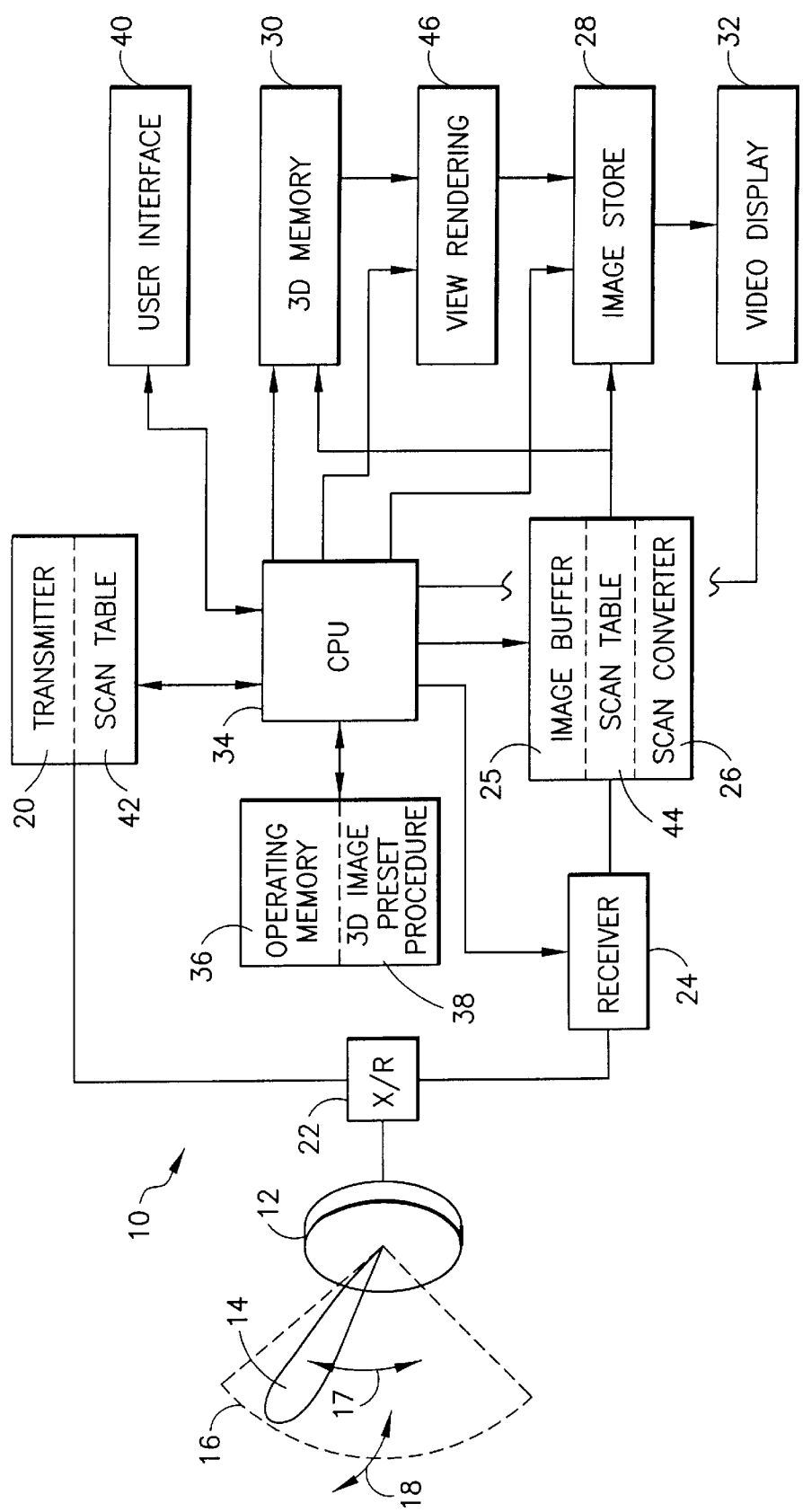
FIG. 3 is a block diagram of a an ultrasound imaging system embodying the invention..

Referring to FIG. 3, ultrasound imaging system 10 includes a transducer 12 that emits an ultrasound beam 14 that is scannable through plane 16. Ultrasound beam 14 is scanned within plane 16 in the directions shown by arrows 17. In addition, through appropriate control signals applied to ultrasound transducer 12, plane 16 can be slewed in the directions shown by arrows 18 so as to enable a full 3-D region to be scanned by ultrasound beam 14.

A transmitter 20 outputs signals to a transmit/receive switch 22 which, in turn, feeds transducer 12 with transmit pulses. In response, transducer 12 emits ultrasound pulses along beam path 14 and receives reflections from anatomical features falling along a scan line which defines the center line of beam 14. The reflections are passed by transmit receive switch 22 to a receiver 24 which, in turn, feeds the signals to scan converter 26. There, polar coordinate echo signal values are stored in a buffer memory 25. The echo signals are then converted to rectangular coordinate image values. The resulting rectangular coordinate image is stored either in an image store 28 or in 3-D memory 30, depending upon the mode of operation of ultrasound imaging system 10.

If it is assumed that ultrasound imaging system 10 is operating in a real time mode, the output from scan converter 26 is passed directly to image store 28. Thereafter, the stored image data is passed from image store 28 to video display 32 for presentation to a viewer. Each of the elements of ultrasound imaging system 10 is controlled by a central processing unit (CPU) 34 which, in turn, utilizes procedures stored in operating memory 36 during its operation. One of the procedures stored in operating memory 36 is a 3-D image pre-set procedure 38 which enables CPU 34 to automatically control the various elements of ultrasound imaging system 10 to display a selected view on video display 32 in accordance with a user input, entered via user interface 40.

Briefly stated, user interface 40 enables a user to select one or more of a plurality of pre-set views that are shown to the user as a listing on video display 32. In response to the user's selection of a listed pre-set view, CPU 34, under control of 3-D view pre-set procedure 38 establishes parameters and conditions within the remaining elements of ultrasound imaging system 10 to automatically enable presentation of the desired pre-set view on video display 32, without further user intervention. User interface 40 also enables the user to simultaneously select plural pre-set views, all of which are automatically derived from an acquired 3-D data set.

To implement this feature of the invention, both transmitter 20 and scan converter 26 are provided with scan tables 42 and 44, respectively, which control their respective elements in accordance with the user's view choice. For example, scan table 42 includes parameters which define a region of interest to be scanned, assuming the positioning of transducer 12 at a position to acquire a 3-D image data set which includes the anatomical feature selected by the user. Accordingly, scan table 42 has a separate set of parameters for control of transmitter 20 for each preset anatomical feature to be imaged.

In similar fashion, scan converter 26 is controlled by scan table 44 in accordance with the user's selected preset view. More specifically, scan table 44 includes, for each pre-set view, a separate set of parameters and control entries to enable scan converter 26 to derive, from an input 3-D data set, a view of the selected anatomical feature.

While a 3-dimensional region of interest (ROI) is defined for each preset anatomical feature, it may occur that the user will wish to either reduce, expand or move the ROI. In such case, the user is enabled to alter the ROI by an appropriate input to CPU 34, via user interface 40. A reduction in the size of the ROI enables succeeding 3-D data sets to be more rapidly acquired and the resulting images to be rapidly presented. U.S. Pat. No. 5,538,003 to Gadonniex et al., assigned to the same assignee as this Application, describes a method for enabling rapid identification of an ROI region on an ultrasound display.

Should the user not wish to utilize one of the available pre-set parameter sets, the user may override the pre-set view procedure 38 and enter desired parameters via user interface 40, for insertion into scan tables 42 and 44. In such case, the 3-D data set which is acquired by scan converter 26 is stored in 3-D memory 30. Thereafter, in an interactive fashion, the user is enabled to alter the control parameters to allow view rendering module 46 to derive images for storage in image store 28. Thus, the user may utilize either pre-set views or derive images from acquired 3-D data sets in accordance with the particular anatomical region that is to be imaged.

Figure 1A:
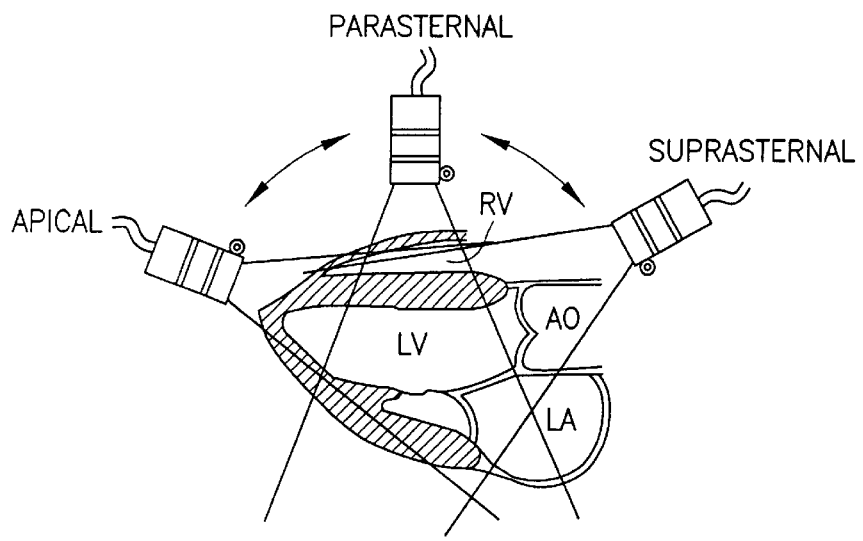
FIG. 1a is a schematic showing of a long-axis view of an ultrasound image of the heart, indicating the imaging orientations from the apical, parasternal and suprasternal positions.
Figure 1B:
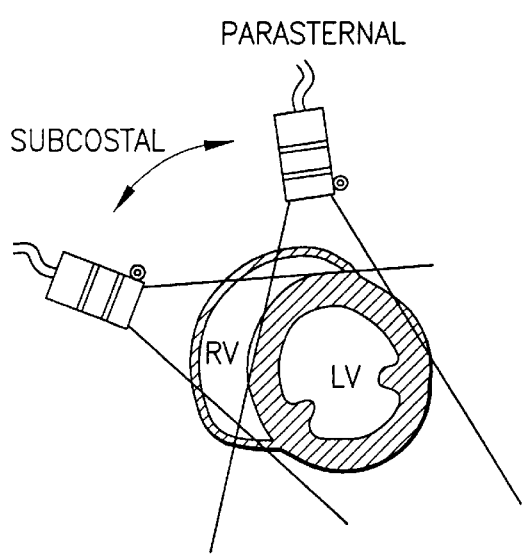
FIG. 1b is a schematic showing of a short-axis view of a heart, taken from either the subcostal or parasternal imaging positions.
Figure 1C:
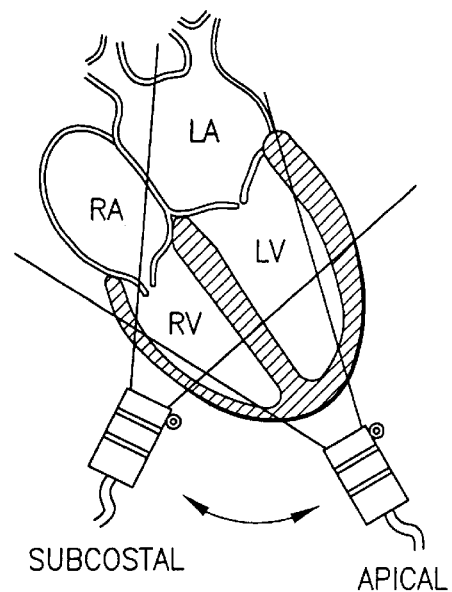
FIG. 1c is a schematic showing of a 4-chamber view a heart with the ultrasound transducer positioned at either the subcostal or apical imaging positions.
Figure 2A:
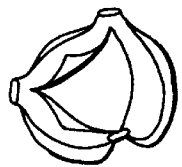
FIG. 2a is a face-on view of the pulmonary valve, in its open state.
Figure 2B:
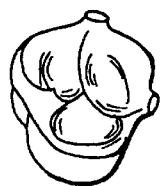
FIG. 2b is a face-on view of the aortic valve, in its closed state.
Figure 2C:
FIG. 2c is a face-on view of the mitral valve, in its closed state.

The provision of the view pre-sets enables the user to acquire views of anatomical elements that are not otherwise available from standard imaging positions on the human anatomy. For instance, one pre-set view may present the face-on view of the mitral valve shown in FIG. 2c without requiring any action on the part of the user other than the proper positioning of ultrasound transducer 12 and the selection of the preset view entitled "mitral valve". Further, in addition to individual views, a "loop" of plural time-lapse views can be derived to enable a film clip-like presentation to the user.

Figure 4:
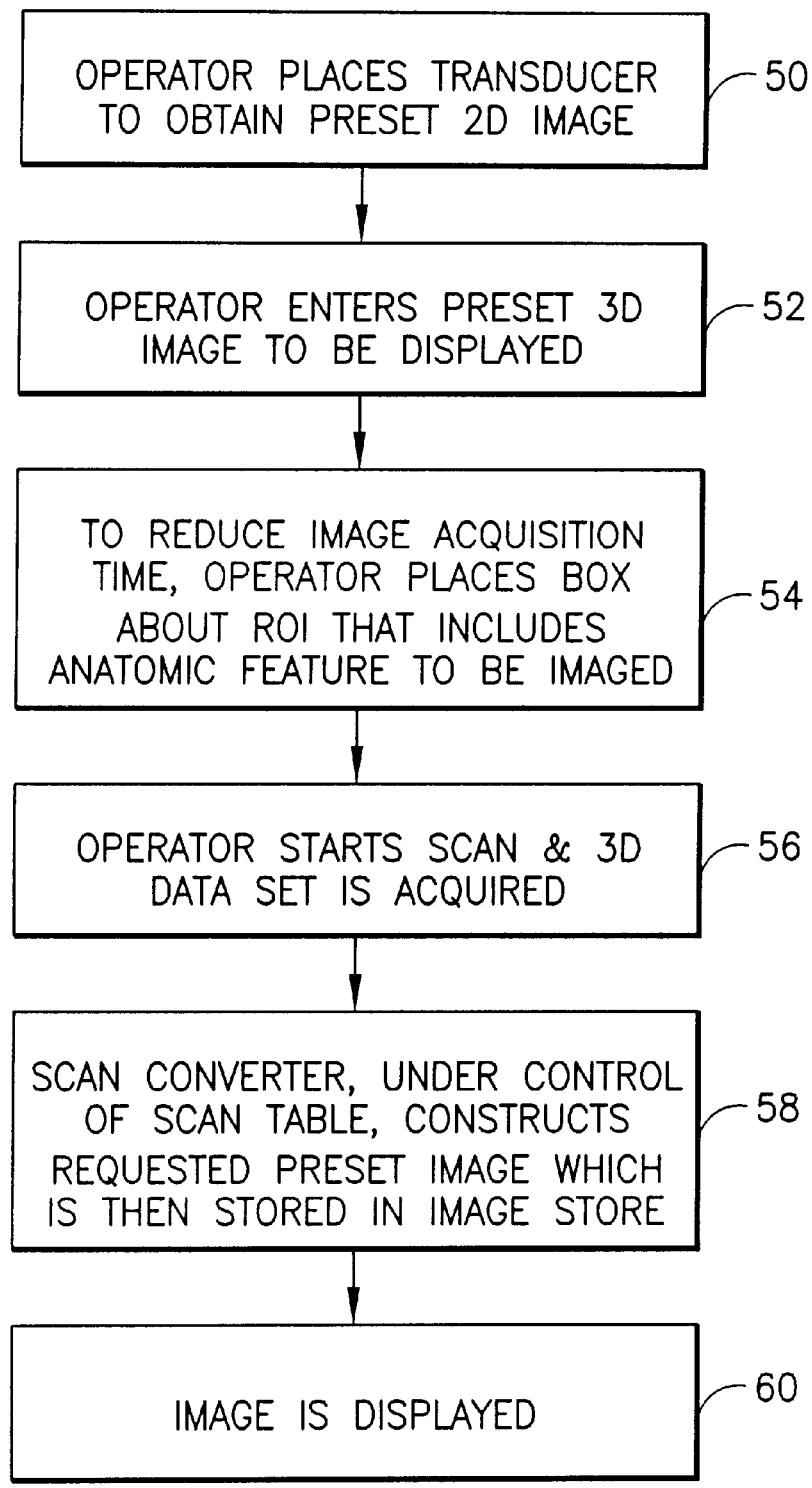
FIG. 4 is a logical flow diagram illustrating the operation of a first embodiment of the invention.

Turning now to FIG. 4, steps 50–60 illustrate the procedure of the invention, when employing user-selected view pre-sets. Initially, the operator places ultrasound transducer 12 to obtain a pre-set 2-D view (step 50). That allows the operator to know that the transducer is in the proper position to acquire an image from a subsequent 3-D scan. The operator then enters a pre-set 3-D view to be displayed (step 52) and may, if reduced image acquisition time is desired, place a box about the ROI to reduce the ultimate data set that is acquired (step 54). Thereafter, the operator starts the scan operation and the 3-D data set is acquired, as above described (step 56). Scan converter 26, under control of scan table 44, constructs the requested pre-set view from the acquired 3-D data set and stores the image in image store 28 (step 58). Thereafter, the image is displayed (step 60).

Figure 5:
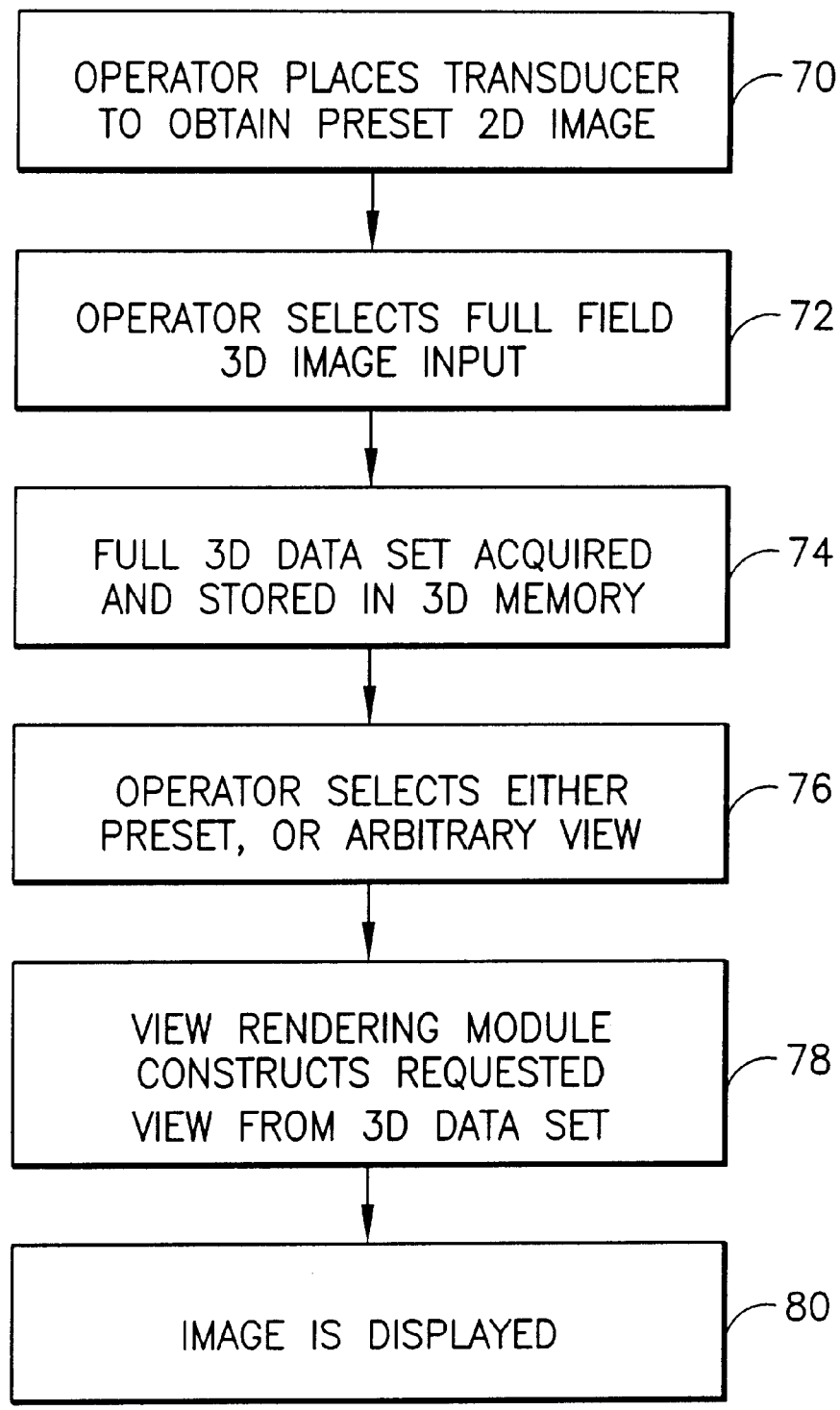
FIG. 5 is a logic flow diagram illustrating the operation of a second embodiment of the invention.

FIG. 5 illustrates the operation of the invention if it is desired to acquire a wide field 3-D data set and then to choose one or more views from that data set on an off-line basis, either on the ultrasound system or on another processor. The procedure starts by instructing the operator to place ultrasound transducer 12 to obtain a pre-set 2-D view (step 70). The operator then selects the full field 3-D view (step 72) and a full 3-D data set is acquired and stored in 3-D memory 30. Thereafter, the operator is enabled to select either a pre-set view or an arbitrary view (step 76) and, in the latter case, to input the necessary parameters to enable CPU 34 to control video rendering unit 46 to construct the desired image. Thereafter, view rendering module 46 produces the requested view from the 3-D data set (step 78) and feeds the image to image store 28, from where it is thereafter displayed by video display 32 (step 80). The view data set may either be derived directly on the ultrasound unit or on another processor to free the ultrasound unit for diagnostic procedures.

It may turn out that the selected pre-set anatomical view does not automatically align with the acquired 3-D data. In such case, CPU 34 can alter scan table 42 to adjust the scan region of ultrasound transducer 12 by looking for edges or surfaces or movement in the data and matching it with a simplified anatomical model of the pre-set view stored in memory 36. Such action can be incorporated into the code contained within 3-D view preset procedure 38. Further, upon selection of a pre-set anatomical view, the user can be requested to place a cursor in the neighborhood of the feature being imaged. That action simplifies that placement of the ROI box.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. An ultrasound imaging system for obtaining anatomical views, said system comprising:
   transducer means for producing an ultrasound beam that is scannable so as to enable acquisition of a 3-D set of image return signals;
   converter means for converting said 3-D set of image return signals to a selected view data set for presentation to a display device;
   a display device for displaying an image representative of said selected view data set;
   user interface means for enabling selection of a preset anatomical view from a set of anatomical views determined by a scanning position of the transducer means; and
   processor means coupled to said transducer means, converter means, display device and user interface means, for enabling said user to be presented with a listing of preset anatomical views, and responsive to a user selection of one of said preset anatomical views, to control said converter means to derive from said 3-D set of image return signals, an image data set which, when displayed, presents the preset anatomical view selected by the user.

2. The ultrasound imaging system as recited in claim 1, wherein said preset anatomical view is not otherwise available from a 2-D scan from standard ultrasound imaging positions.

3. The ultrasound imaging system as recited in claim 1, wherein said user interface means enables a user input to restrict a volume to be scanned by said ultrasound transducer to a region encompassing anatomy to be shown by said preset anatomical view.

4. The ultrasound imaging system as recited in claim 3, wherein said user input constitutes placement of a cursor at an anatomical feature, said cursor placement controlling placement of said volume to be scanned by said ultrasound beam.

5. The ultrasound imaging system as recited in claim 1, wherein said processor means, in response to said selection by said user, automatically restricts a volume to be scanned by said ultrasound beam to a region encompassing anatomy to be shown by said selected preset anatomical view.

6. The ultrasound imaging system as recited in claim 1, wherein said processor means, in response to said selection by said user, automatically invokes plural view parameters, including at least one of: a parameter to control a volume to be scanned by said ultrasound beam, a parameter defining a viewpoint from which said selected preset anatomical view is to be seen, and a parameter controlling image magnification.

7. The ultrasound imaging system as recited in claim 1, wherein said processor means compares an acquired preset anatomical image with an anatomical model and adjusts parameters of said acquired preset anatomical view to correct a mismatch with said anatomical model.

8. The ultrasound imaging system as recited in claim 1, wherein said user interface means enables a user to select a set of plural preset anatomical views and said processor means responds by automatically deriving from said 3-D data set, said set of plural preset anatomical views without further user intervention.

9. A method for controlling an ultrasound imaging system to obtain ultrasound views, said system including a transducer for producing an ultrasound beam that is scannable so as to enable acquisition of a 3-D set of image return signals, an image converter for converting the 3-D set of image return signals to a selected image data set for presentation to a display, and a display device for displaying a view representative of the image data set, said method comprising:
   a) presenting a listing of preset anatomical views that may be selected based on a position of the transducer during a scanning operation;
   b) responding to a user selection of one of said preset anatomical views, by controlling said image converter to derive from said 3-D set of image return signals, an image data set that includes return signal data from a region including an anatomical feature to be included in said preset anatomical view; and
   c) displaying the preset anatomical view selected by the user.

10. The method as recited in claim 9, wherein said preset anatomical view is not otherwise available from a 2-D scan from standard ultrasound imaging positions.

11. The method as recited in claim 9, wherein step b) further responds to a said user selection by restricting a volume scanned by said ultrasound transducer to a region encompassing anatomy to be shown by said preset anatomical view.

12. The method as recited in claim 9, wherein said user selection includes placement of a cursor at a displayed anatomical feature, said cursor placement controlling placement of said volume to be scanned by said ultrasound transducer.

13. The method as recited in claim 9, wherein step b) in response to said selection by said user, automatically invokes plural view parameters, including at least one of: a parameter to control a volume to be scanned by said ultrasound beam, a parameter defining a viewpoint from which said selected preset anatomical view is to be seen, and a parameter controlling image magnification.

14. The method as recited in claim 9, wherein step c) further responds to a user selecting a set of plural preset anatomical views by automatically deriving from said image data set, said set of plural preset anatomical views without further user intervention.

15. A three-dimensional ultrasound system comprising:
   a transducer unit responsive to values in a scan table for scanning a body;
   a memory storing the scan table; and
   a control circuit which displays a list of anatomical views to a user and, upon selection of an anatomical view by the user, utilizes a sub-set of the scan table so as to acquire a data set from which the anatomical view selected by the user can be displayed in real time.

16. An ultrasound system, as set forth in claim 15, further comprising:

a scan converter that, responsive to the scan table, constructs an image of the selected anatomical view based on data from the transducer.

17. An ultrasound system, as set forth in claim 15, wherein the scan table comprises:

a first scan table containing parameters to control a transmit function of the transducer unit; and a second scan table containing parameters to control a receive function of the scan converter.

18. An ultrasound system, as set forth in claim 15, wherein the scan converter constructs an image of the selected anatomical view based on 3-D data.

19. An ultrasound system, as set forth in claim 15, wherein the scan converter constructs an image of the selected anatomical view based on 2-D data.

20. An ultrasound system, as set forth in claim 15, wherein the preselected views include at least one of: a face-on view of the pulmonary valve view; an aortic valve view; a tricuspid value view; and a mitral valve view.

21. An ultrasound system, as set forth in claim 15, wherein the transducer is a two dimensional array transducer.

22. An ultrasound system, as set forth in claim 15, wherein the control circuit identifies a sub-set of the scan table to utilize based on a volume to be scanned.

23. A method of conducting an ultrasound examination comprising:

placing a two-dimensional array transducer next to an examination subject;

identifying an examination position of the two-dimensional array transducer;

displaying a list of anatomical views available for display based on the examination position of the two-dimensional array transducer;

indicating one of the anatomical views from the list of anatomical views;

obtaining ultrasound data from the two-dimensional array transducer for producing the indicated anatomical view; and creating an image corresponding to the indicated anatomical view from the ultrasound data.

24. A method, as set forth in claim 23, wherein the step of identifying an examination position comprises receiving an indication from the user of the examination position.

25. A method, as set forth in claim 23, wherein the step of identifying an examination position comprises analyzing data from the two-dimensional array transducer.

26. A three-dimensional ultrasound system comprising:

a transducer unit that scans a body; and a control circuit which displays a list of anatomical views to a user based on a position of the transducer unit during the scanning of the body and, upon selection of an anatomical view by the user, acquires a data set from data output by the transducer unit from which the anatomical view selected by the user can be displayed.

27. An ultrasound system, as set forth in claim 26, wherein the control circuit selects the anatomical view for inclusion in the list of anatomical views based on a scanning position of the transducer.

\* \* \* \* \*